(12) United States Patent
Black

(10) Patent No.: US 6,953,341 B2
(45) Date of Patent: Oct. 11, 2005

(54) TOOTHPICK FOR LIGHT TREATMENT OF BODY STRUCTURES

(75) Inventor: Michael Black, Foster City, CA (US)

(73) Assignee: Oralum, LLC, Foster City, CA (US)

( * ) Notice: Subject to any disclaimer, the term of this patent is extended or adjusted under 35 U.S.C. 154(b) by 52 days.

(21) Appl. No.: 10/645,674

(22) Filed: Aug. 20, 2003

(65) Prior Publication Data

US 2004/0116985 A1 Jun. 17, 2004

(51) Int. Cl.$^7$ .............................. A61C 3/00; A61C 13/00
(52) U.S. Cl. ............................................ 433/29; 132/321
(58) Field of Search ........................... 433/29, 215, 216; 132/321, 323–324, 329; 606/13–16

(56) References Cited

U.S. PATENT DOCUMENTS

| | | | |
|---|---|---|---|
| 5,055,048 A | 10/1991 | Vassiliadis et al. | 433/215 |
| 5,090,908 A | 2/1992 | Teumim-Stone | 433/215 |
| 5,271,734 A * | 12/1993 | Takeuchi | 433/72 |
| 5,342,198 A | 8/1994 | Vassiliadis et al. | 433/215 |
| 5,423,677 A * | 6/1995 | Brattesani | 433/72 |
| 5,435,724 A | 7/1995 | Goodman et al. | 433/215 |
| 5,456,603 A | 10/1995 | Kowalyk et al. | 433/215 |
| 5,795,153 A | 8/1998 | Rechmann | 433/216 |
| 6,019,605 A | 2/2000 | Myers | 433/215 |
| 6,026,828 A | 2/2000 | Altshuler | 132/311 |
| 6,304,712 B1 * | 10/2001 | Davis | 385/147 |
| 6,569,156 B1 | 5/2003 | Tankovich et al. | 606/10 |
| 6,613,042 B1 | 9/2003 | Tankovich et al. | 606/10 |
| 6,758,844 B2 | 7/2004 | Neuberger | 606/3 |
| 2004/0193236 A1 | 9/2004 | Altshuler et al. | 607/88 |

FOREIGN PATENT DOCUMENTS

WO    WO 01/12095 A1    2/2001

OTHER PUBLICATIONS

2001/0023057, Sep. 20, 2001, Alexander, "Device For Identifying Caries, Plaque, Bacterial Infectrion, Concretions, Tartar And Other Fluorescent Substances On Teeth".

* cited by examiner

Primary Examiner—Cary E. O'Connor
(74) Attorney, Agent, or Firm—Lumen Intellectual Property Services, Inc.

(57) ABSTRACT

A toothpick for the application of light treatment at a body structure is provided. The toothpick distinguishes a handle and an element. The handle hosts one or more light sources each capable of delivering a light beam with a unique light treatment. The element is optically connected to the light source(s) such that the light beam(s) could radiate through the surface of the element at a body structure. This radiation is not limited to radiation through the tip of the element, but would radiate in multiple directions. The element of the toothpick could be used in direct or not in direct contact with a body surface as long as the light treatment can be applied to the body structure. In case the element is in contact with a body structure, then the element could add a massaging effect to the body structure.

46 Claims, 16 Drawing Sheets

TOOTHPICK FOR LIGHT TREATMENT OF BODY STRUCTURES

FIELD OF THE INVENTION

This invention relates generally to toothpicks. More particularly, the present invention relates to toothpicks capable of providing hygienic effects.

BACKGROUND

In general, hygiene relates to the principles of cleanliness, promotion and preservation of health or the freeing from disease-causing microorganisms. Hygienic effects can be established in different ways of which one is through the effect of light on biological structures. For instance, the hygienic effect of visible, near ultraviolet and infrared light on biological structures is known and has been described to provide anti-inflammatory effects, preventative effects, caries-protective effects, heating effects, anti-bacterial effects, sterilizing effects, cleaning effects, cosmetic effects, therapeutic effects, healing effects, bio-stimulative effects, bio-altering effects, pain-releaving effects, agent-penetrating effects, photo-rejunivating effects and photo-dynamic treatment effects (See for instance a book by Goldman (1981) entitled *"The biomedical laser: technology and clinical applications"* and published by Springer-Verlag, New York; a book by Katzir (1993) entitled *"Lasers and optical fibers in medicine"* and published by Academic Press, New York; a book by Hajder et al. (1994) entitled *"Acupuncture and lasers"* and published by Ming, Belgrade; a book by Tuner et al. (1996) entitled *"Laser therapy in dentistry and medicine"* and published by Prisma Books, Grangesberg, Sweden; a book by Alster et al. (1996) entitled *"Cosmetic laser surgery"* and published by Wiley & Sons, New York; or a book by Fitzpatrick et al. (2000) entitled *"Cosmetic Laser Surgery"* and published by Mosby, St. Louis). The effects of a laser light on biological structures is dependent on the laser properties (active matter, beam wavelength, continuous or impulse mode of operation), characteristics of the structures, water content, pigmentation degree, vascularization, vitality, heterogeneity, specific heat conductivity or time exposure. The photo-effect of a laser can be applied to superficial structures and subcutaneous structures. As far as the mechanisms of laser radiation effects are concerned, they may be thermal, mechanical or chemical.

When it comes to oral hygiene, the art teaches a wide variety of toothpicks in various shapes. Generally, a toothpick is a small pointed piece of wood or plastic for removing substances. Toothpicks are especially known to remove food particles from between the teeth. In this sense toothpicks contribute to the overall hygiene of a person's oral cavity and in particular the teeth. However, the use of such toothpicks would not necessarily prevent that person from diseases or health deterioration of the structures in an oral cavity. More generally, a toothpick would not be able to provide hygienic effects that could be provided by the application of light. Accordingly, there is a need for new toothpicks that would be able to provide a more comprehensive application of hygienic effects to oral cavities and body cavities in general.

SUMMARY OF THE INVENTION

The present invention provides a toothpick for light treatment at a body structure. The toothpick distinguishes a handle and an element. The toothpick could be developed as one single piece. However, the toothpick could also be developed with removable, disposable, reusable or replaceable parts, i.e. for instance the handle and/or element. The handle hosts one or more light sources each capable of delivering a light beam with a unique light treatment. The element is optically connected to the light source(s) such that the light beam(s) could radiate through the surface of the element at a body structure. This radiation is not limited to radiation through the tip of the element, but would radiate in multiple directions.

In one aspect, the element is a transparent element and the light beam radiates substantially through the entire surface of the transparent element. In another aspect, the element is a non-transparent element and optical guides could then be included within the element in such a way that the radiation of the light beam passes the surface of the element in multiple directions. In yet another aspect, the element could be a transparent element with optical guides whereby the optical guides promote the propagation of the light beam through the transparent element. In still another aspect, the element could include optical components (e.g. reflective grooves) to promote the propagation of the light beam.

The element could take different shapes. In one aspect, the element is slender and elongated. For instance, the element could be tapered or cone-shaped. In another aspect, the element could include different shapes, the selection which could be dependent on for instance the desired appearance of the toothpick, preference by the user or manufacturer, and/or type of application (e.g. area of treatment or location of treatment). Examples of such shapes are a bead-shape at the tip of the element or a flat shaped head. In another aspect, the element could have texture (e.g. ribbed surface or a bubbled surface) or could have bristles. The texture or bristles could be transparent to the selected light beam, could include one or more optical guides, or could be non-transparent. The element could also be made out of material(s) that is (are) bendable or formable. The element could be developed with a pre-arranged angle or if bendable or formable material(s) is (are) used then the user could manipulate the element to create any desired angle of the element.

The light source could be a low power laser, a light emitting diode or a semiconductor laser to provide a light beam from the ultraviolet, visible or infrared spectrum. The types of light treatments that could be selected could include any of the following effects, such as an anti-inflammatory effect, a preventative effect, an anti-bacterial effect, a sterilizing effect, a heating effect, a caries-protective effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect. The light source could be controlled in a pulsed manner and a continuous manner. It would also be possible to control one or more parameters of the light source and therewith the light treatment. Examples of how such a light treatment could be changed or updated are discussed.

The element of the toothpick could be used in direct or not in direct contact with a body surface as long as the light treatment can be applied to the body structure. In case the element is in contact with a body structure, then the element could add a massaging effect to the body structure. In addition, the toothpick could include different kinds of massaging means. For instance, the texture, the different shapes or the bristles could contribute to this massaging effect. Furthermore, the toothpick could include a vibrating means to add a massaging effect.

In one variation, the toothpick could be combined with a floss, e.g. a dental floss, that could be (removable, disposable, reusable or replaceable) attached to the handle. In one aspect the floss could be a transparent floss, which is optically connected to a light source to radiate a light beam with a selected light treatment through the transparent floss at a body structure. In another variation an agent could be used and applied to the body structure before, during or after the application of the light treatment. Such agents could work as a catalyst, soother or enhancer to the body structure.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Figure 1:
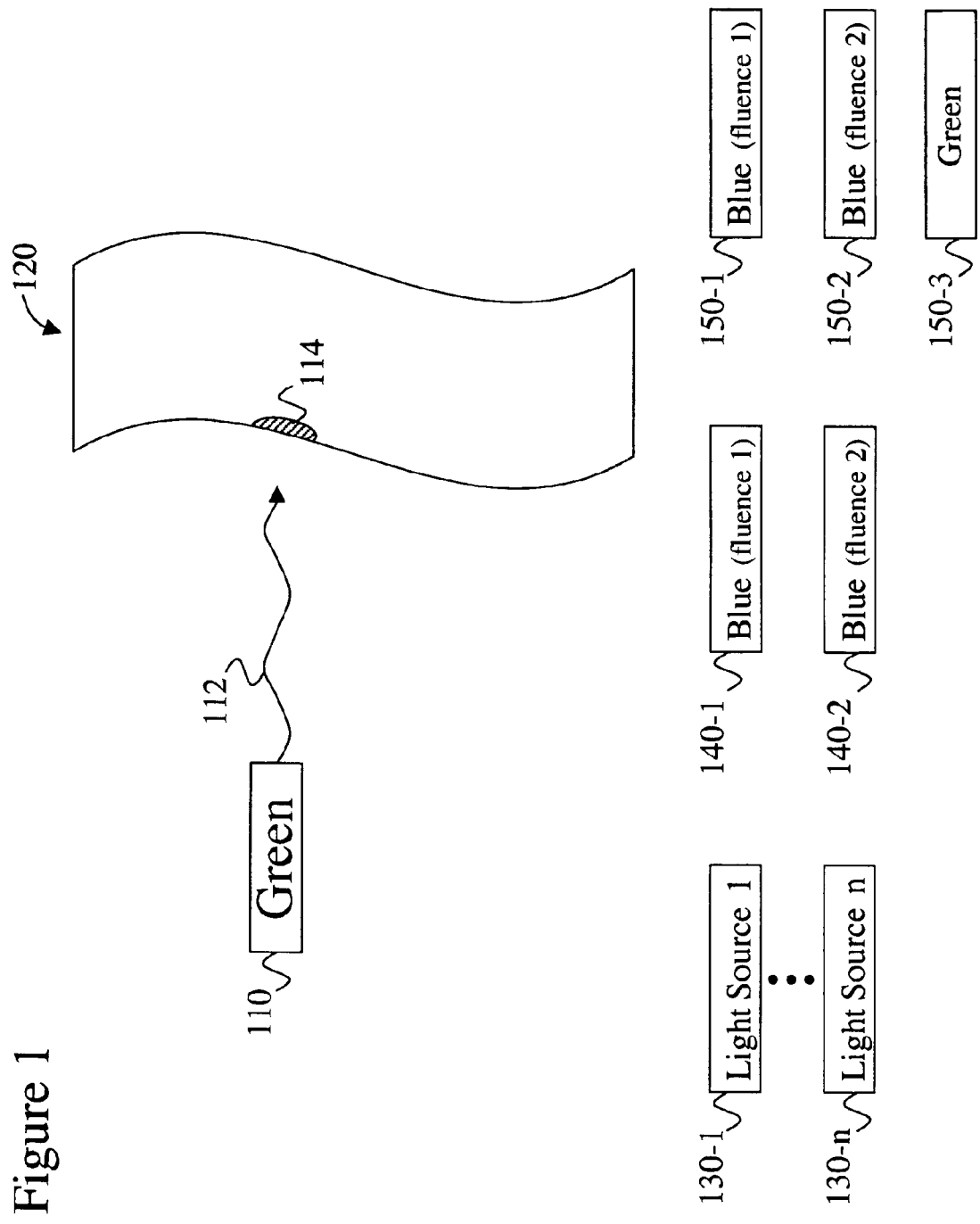
FIG. 1 shows examples of applying hygienic effects to body structures in a quasi-stationary manner according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a toothpick capable of applying one or more light treatments to body structures. These light treatments are established by one or more light sources each capable of delivering a light beam with a unique light treatment to the body structures. The application of the light treatments could be established either in a quasi-stationary manner or a dynamic manner. The light sources are preferably low power light sources including low power lasers, light emitting diodes or low power semiconductor lasers (See, for instance, the following companies which are listed for purposes of illustration and should not be regarded as limiting to the invention: Coherent Inc., Santa Clara, Calif.; Microlasers by PolyScientific Inc., Blackbury, Va.; Photonic Products, Bishops Stortford, United Kingdom; Organic LEDs by Covion Organic Semiconductors GmbH, Frankfurt, Germany; Blue light emission from porous silicon by University of Science and Technology of China in Hefei). The desired light treatment(s) that one would like to obtain guides the choice of the light source (light sources) and the parameter(s). By varying parameters such as e.g. fluence, spot size, mode such as continuous or pulsed, repetition rate, pulse duration different light treatments could be established.

A body structure is defined as any body structure that was created in a natural way, created in an unhealthy way or created in an unnatural way. Examples of naturally created body structures for which the toothpick of the present invention could be useful are the oral system or mouth, a nasal system or nose, an ear, a vaginal system, uterus or a rectal system. Examples of an unhealthy created body structure for which the toothpick of the present invention could be useful are body structures that are caused by disease or infections. Examples of unnaturally created body structures for which the toothpick of the present invention could be useful are open wounds, gunshot wounds that created a structure, open wounds inflicted by physical assault, burns that created a structure, or surgically created body structures, including body structures created with an endoscope. A surgically created body structure is, for instance, created by an incision through the skin such that the skin opening provides access to subcutaneous body structures that might require hygienic treatment. Examples of surgically accessible body structures include the cardio-vascular system, intestinal system, organs, or any other body structures surrounding the organs or functional systems. Body structures encompass any type of microorganism (including disease-causing microorganisms), cell layers, tissues, organs, teeth or materials as well as any type of non-biological materials that are present in a body structure including fillings, braces, medical assistive devices, medical preventive devices, or the like.

In general, light treatments are defined as treatments with hygienic effects that relate to the cleanliness of these structures, promotion and preservation of health of the structures, freeing the body structure from disease-causing microorganisms or providing therapeutic effects. In particular, the present invention encompasses hygienic effects related to the hygienic effect of visible, near ultra-violet and infrared light on these structures, which are known in the art (for a light spectrum refer to page 13 in a book by Tuner et al. (1996) entitled *"Laser therapy in dentistry and medicine"* and published by Prisma Books, Grangesberg, Sweden). Examples of such hygienic effects that could be selected include anti-inflammatory effects, preventative effects, caries-protective effects, heating effects anti-bacterial effects, sterilizing effects, cleaning effects, cosmetic effects, therapeutic effects, healing effects, bio-stimulative effects, bio-altering effects, pain-releaving effects, teeth whitening effects, photo-rejuvination effects, photodynamic effects or agent-penetration effects.

To establish a particular hygienic effect at a body structure one needs to consider the light source properties such as the type of low power light source, wavelength of the light beam, the continuous or impulse mode of operation of the light sources, characteristics of the structures, water content of the structures, pigmentation degree of the structures, vascularization of the structures, vitality of the structures, heterogeneity of the structures, specific heat conductivity of the structures, the fluence of light penetration through a structure or the time exposure needed for the light beam. The art provides teachings on hygienic photo-effects of structures including guidelines regarding parameters such as the type of light source, selection of wavelength(s), fluence, penetration, selection of spot size, recommended pulse duration, recommended repetition rate, or the like. The selection of the hygienic effect as part of the present invention incorporates these teachings as well as new teachings that become available in the art describing newly identified hygienic effects.

Currently available teachings are described in the following books, which provide an exemplary list rather than a comprehensive list. The list includes a book by Goldman (1981) entitled *"The biomedical laser: technology and clinical applications"* and published by Springer-Verlag, New York; a book by Katzir (1993) entitled *"Lasers and optical fibers in medicine"* and published by Academic Press, New York; a book by Hajder et al. (1994) entitled *"Acupuncture and lasers"* and published by Ming, Belgrade; a book by Tuner et al. (1996) entitled *"Laser therapy in dentistry and medicine"* and published by Prisma Books, Grangesberg, Sweden; a book by Alster et al. (1996) entitled *"Cosmetic laser surgery"* and published by Wiley & Sons, New York; or a book by Fitzpatrick et al. (2000) entitled *"Cosmetic Laser Surgery"* and published by Mosby, St. Louis).

FIG. 1 shows a first exemplary embodiment of a light source 110 delivering a light beam with a green wavelength 112. The green wavelength 112 provides a unique hygienic effect when applied to body structure 120. In this example, light beam 112 has a fairly superficial hygienic effect at body structure 120 as shown by 114. In general, one or more light sources could be used such as n light sources 130-1 to 130-n. Two of the same light sources could be used such as two light sources 140-1, 140-2 that each deliver blue light, however, with at least one different parameter to establish a different and unique hygienic effect for each of the two light sources 140-1, 140-2. Such a different and unique hygienic effect could be established by different fluences for each of the two light sources 140-1, 140-2, i.e. fluence 1 and fluence 2, respectively. The relative subsurface fluence of a light beam in a structure is dependent on the spot size, which could be relatively small or relatively large. The same subsurface fluence values appear at deeper levels with the larger spot size compared to the smaller spot size. Another example is that there are three light sources, of which two are the same 150-1, 150-2 and one 150-3 is different, though all three delivering a unique hygienic effect.

Figure 2:
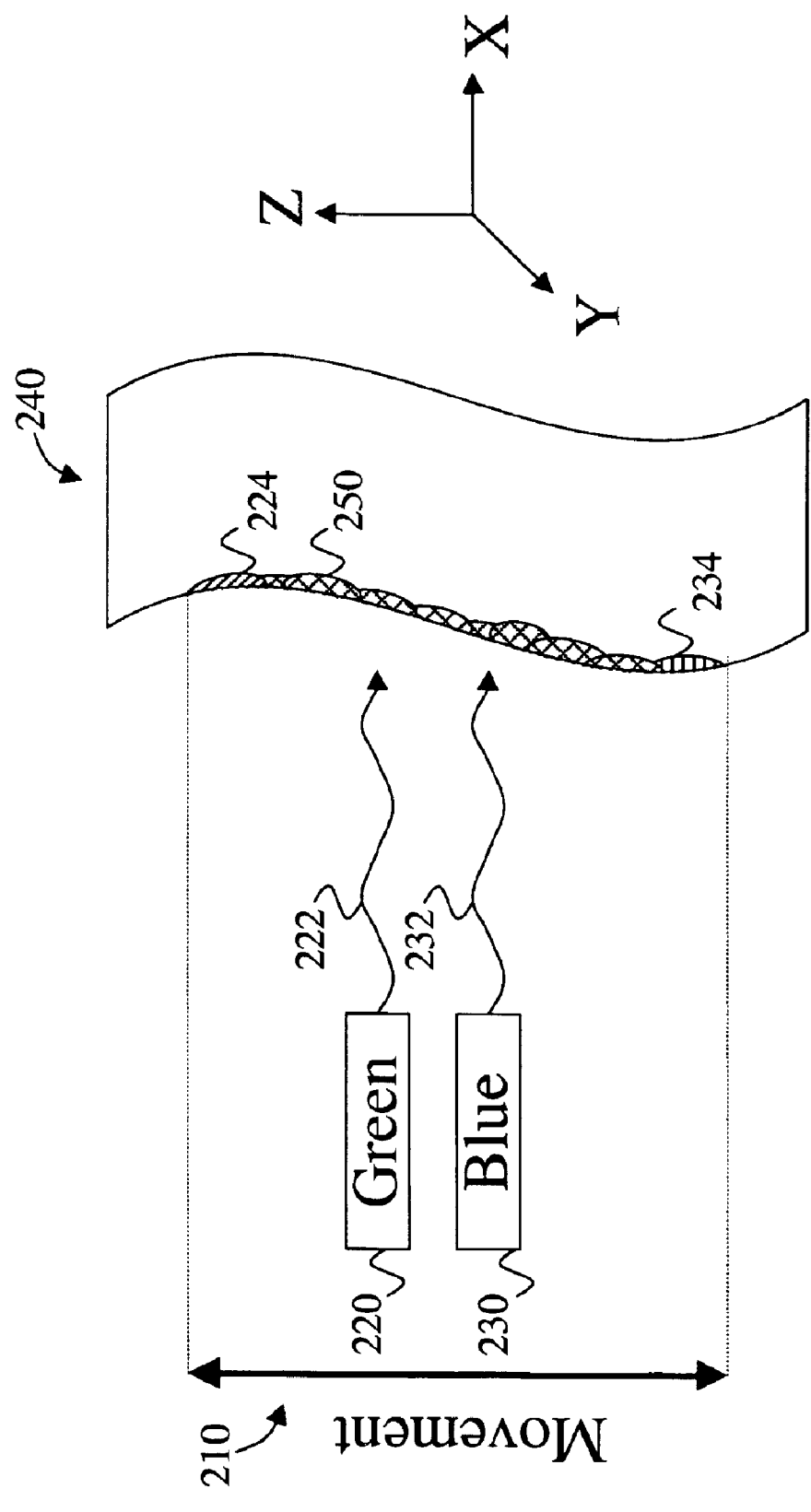
FIGS. 2–3 shows examples of applying hygienic effects to body structures in a dynamic manner according to the present invention.
Figure 3:
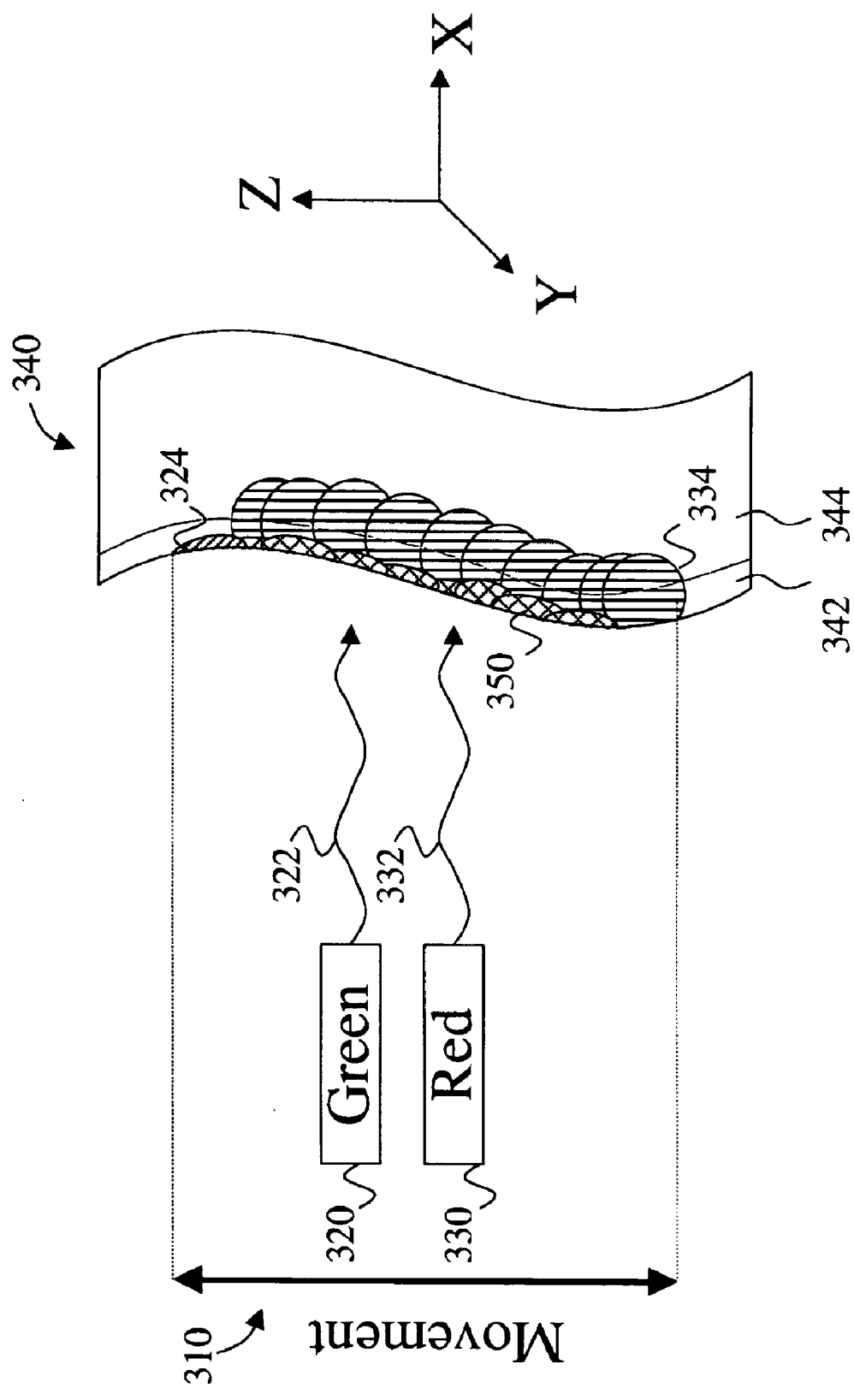

FIG. 1 shows an exemplary embodiment of different hygienic effects in a structure in which the light beams are applied in a quasi-stationary manner. FIGS. 2–3 show exemplary embodiments of the application of hygienic effects in a dynamic manner. Movement 210 of light sources 220, 230 concurrently applies light beam 222, 232 with respectively hygienic effects 224, 234 to different locations at body structure 240 to achieve blending of these two unique hygienic effects at these different locations; 250 is an example of a blended hygienic effect of light beams 222, 232 as a result of movement 210, which is a blend at body structure 240 of blue and green light.

Movement 310 of light sources 320, 330 concurrently applies light beam 322, 332 with respectively the hygienic effects 324, 334 to different layers 342, 344 at body structure 340 to achieve blending of these two unique hygienic effects at the different locations where some of the areas of penetration overlap; 350 is an example of a blended hygienic effect of light beams 322, 332 as a result of movement 310, which is a blend at body structure 340 of red and green light. Note that there are areas where the hygienic effects do not blend together due to different penetration areas, though these hygienic effects are applied in a concurrent fashion. The movement relative to the body structures is not limited to movement 210, 310 (i.e. Z translation), but could be applied in X, Y, or Z direction (translation/rotation).

Figure 4:
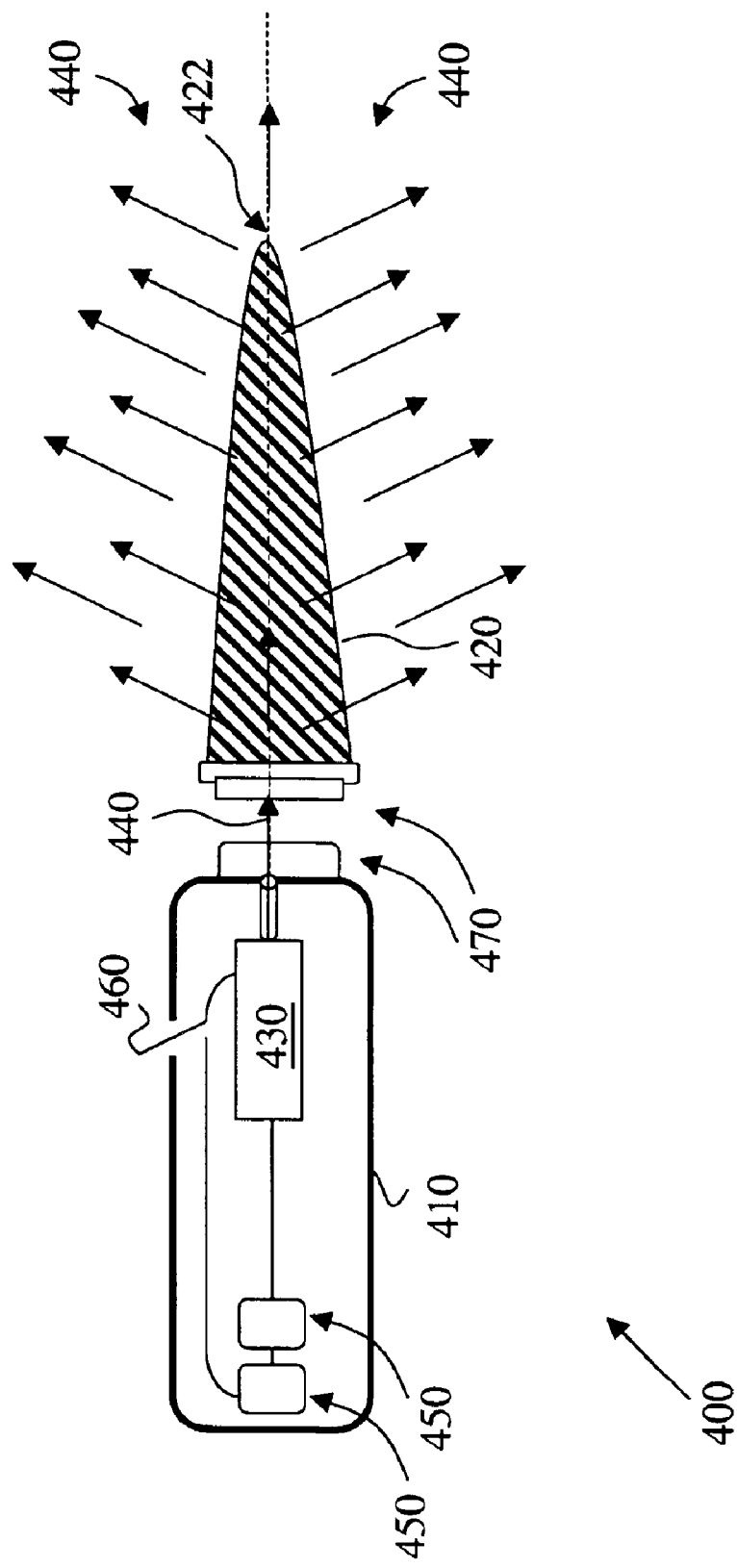
FIG. 4 shows an example of a toothpick according to the present invention.
Figure 5:
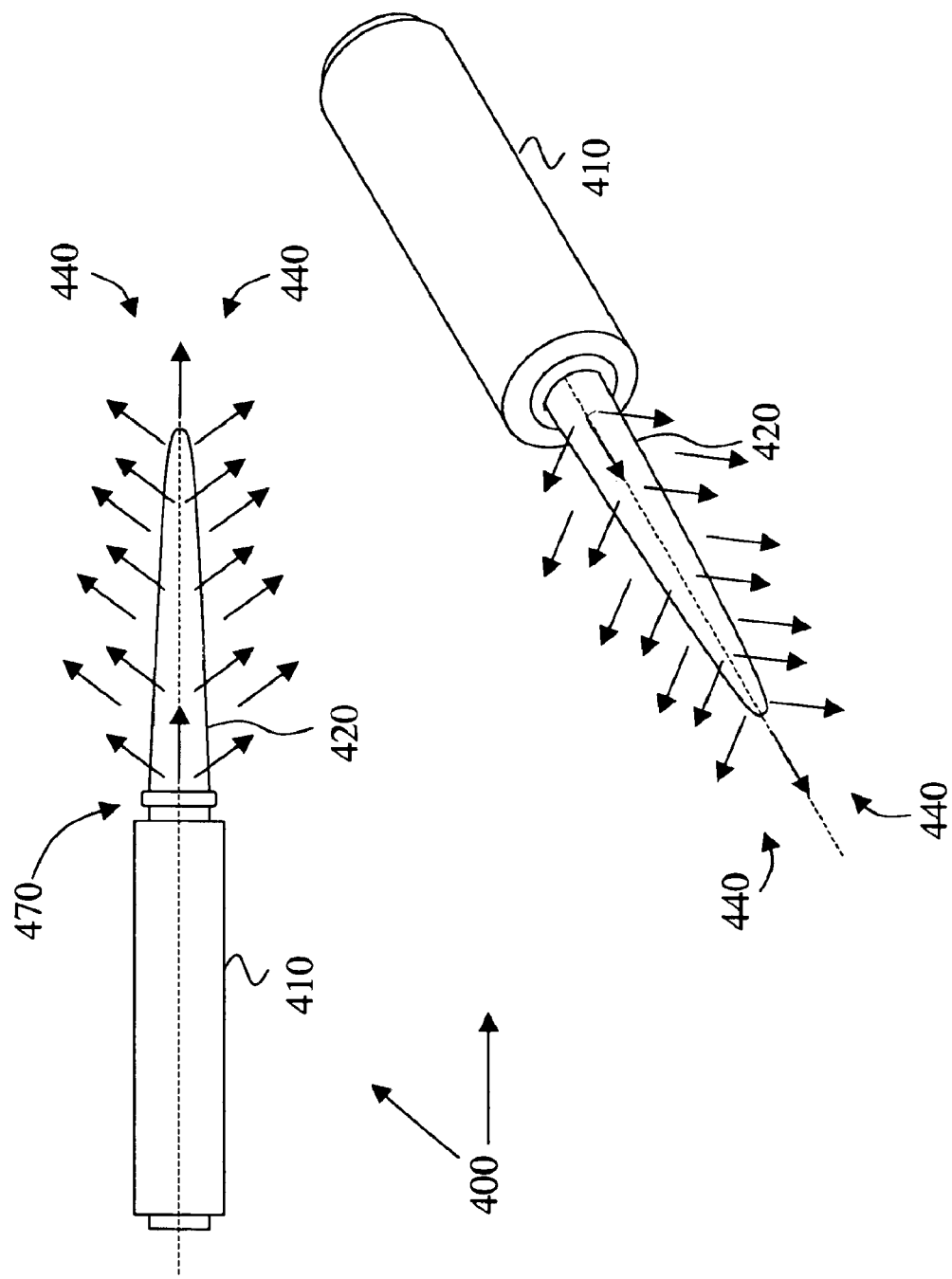
FIG. 5 shows an example of an assembled toothpick according to the present invention.

FIGS. 4–5 show examples of a toothpick 400 that includes a handle 410 and an element 420. Handle 410 hosts a light source 430, which is capable of delivering a light beam 440. Light source 430 is powered by a power supply 450, such as a (rechargeable) battery. Power supply 450 is connected to a switch 460. Switch 460 is preferably positioned at the outside of handle 410 (e.g. at a side or bottom) and controls the on/off stage of power supply 450 and therewith the on/off stage of light source 430.

Element 420 is optically connected to light source 430. In the example of FIG. 4, element 420 is a slender and elongated element. Element could be between 1–5 mm in diameter and between 10 and 80 mm in length. In one aspect element could be made out of transparent material (indicated by the slanted lines in element 410). The transparent material should be capable of propagating the light beam 440 through its body and pass its surface. This would allow the light beam to radiate in various different directions (indicated by the arrows 440). Light beam is not limited to a linear path with respect to the output direction of the light source (indicated by the dashed line), which would only output the light beam through the tip 422 of element 420. Once illuminated, element 420 becomes a glowing element that radiates a selected light treatment. Generally speaking, the light beam radiates substantially through the entire surface of the transparent element and could be used at a distance or in direct contact with a body structure.

Transparent materials suitable for element 420 are materials capable of radiating a selected light beam 440 through the surface of element 420 without loosing the desired treatment effect or power of the light beam. Examples of such a transparent material are for instance, but not limited to, a silicone, a (soft) plastic, a latex, or the like.

In one aspect, handle 410 and element 420 could be two separate parts of toothpick 400, which could be removably attached through an attachment means 470. Such an attachment means 470 could be any type of mechanism known in the art that would not obstruct the optical connection or propagation of the light beam and could be a screw-type connection, a male-female connection, a click connection, or the like. Handle and/or element could be used as a disposable resuasable or replacable element(s). For instance, the element could be replaced with a new element, different style element or a different shape element. Instead of two separate parts, the toothpick could also be manufactured as a single device with a permanent connection between the handle and the element.

The handle could take any shape and is not limited to the shape of handle 410 as shown in FIG. 4. However, it would be preferred to have an ergonomically shaped handle that easily fits a user's hand. Different shapes and sizes of handles would then accommodate the shapes and sizes of the hands of children and adults.

Figure 6:
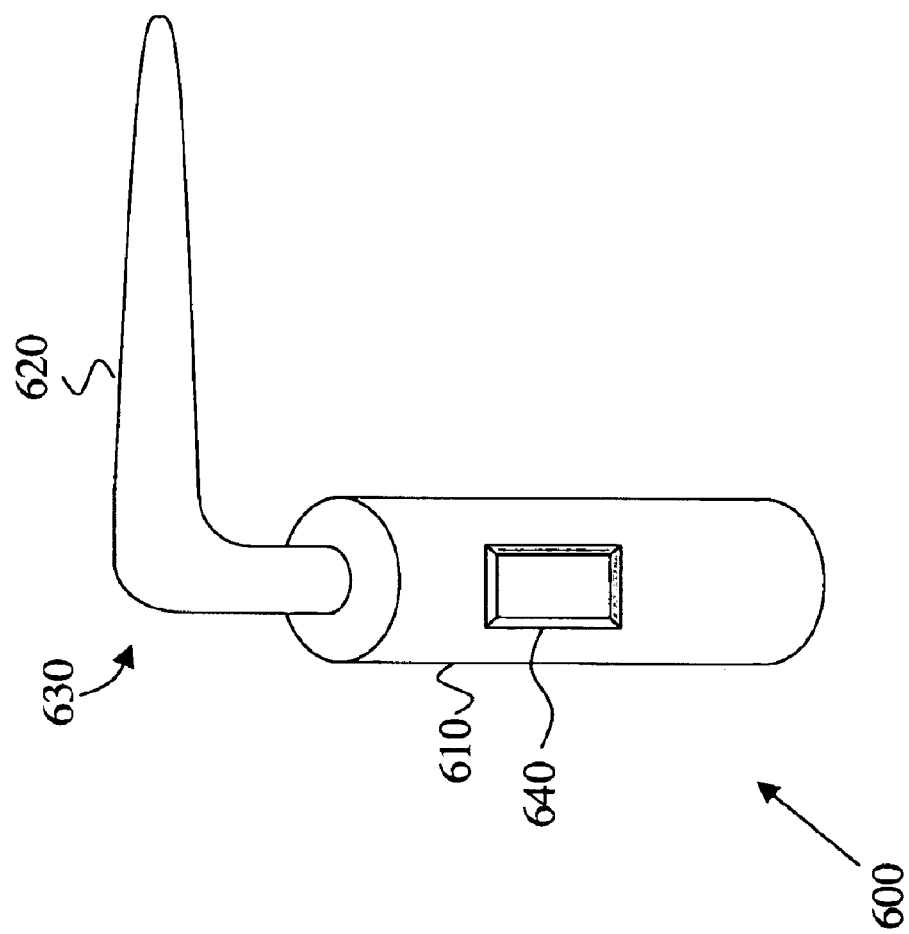
FIG. 6 shows an example of a toothpick with an angled element according to the present invention.
Figure 7:
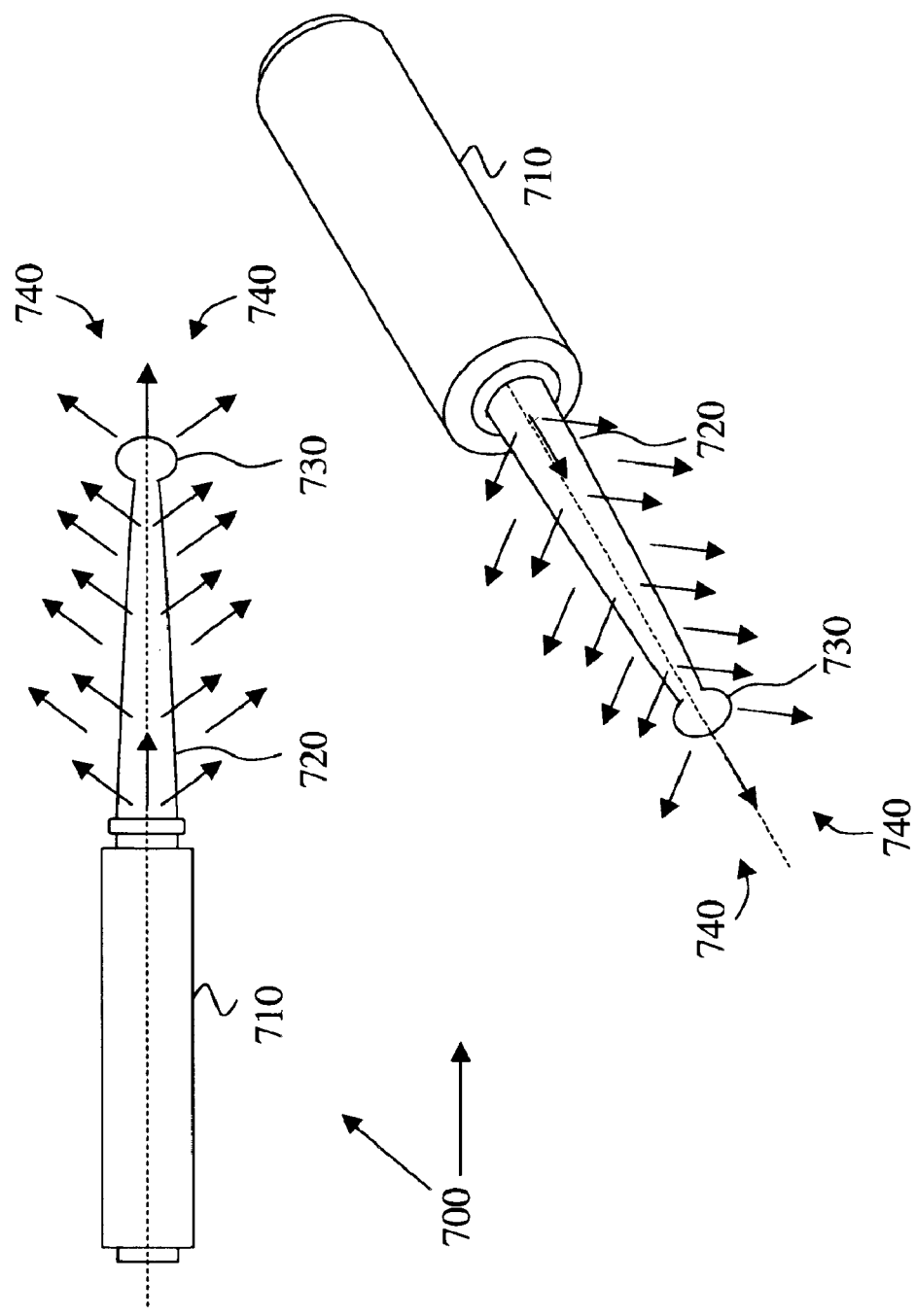
FIG. 7 shows an example of a toothpick with a bead shape tip according to the present invention.
Figure 8:
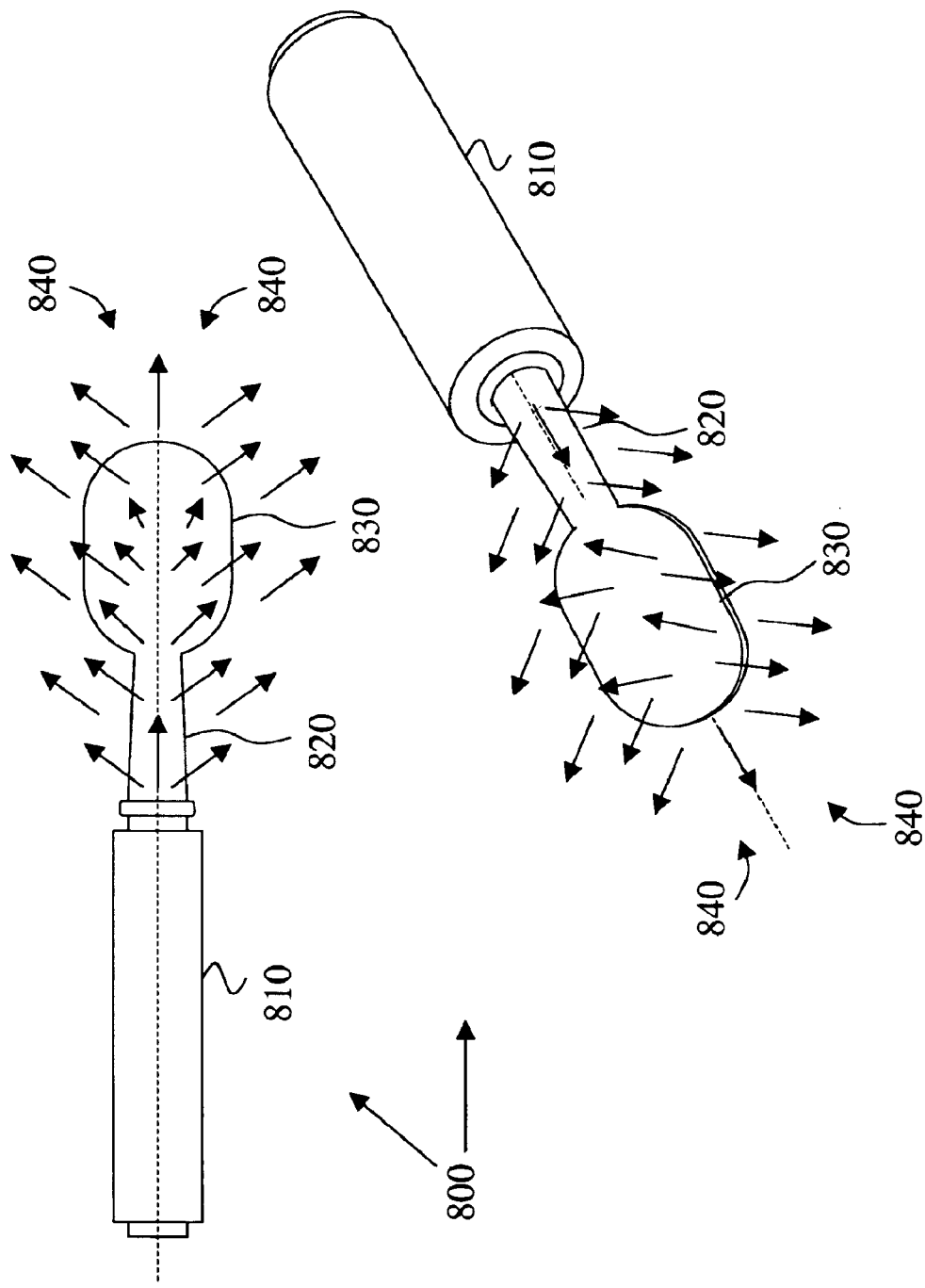
FIG. 8 shows a toothpick with a flat shaped head according to the present invention.

FIGS. 4–5 show the shape of the element in a tapered shape or cone shape. However, as a person of average skill in the art would readily appreciate, the shape of the element could be changed or varied. The shape of the element could either be pre-arranged or formed due to the flexibility of the material of the element. The choice of the shape or shape changes of the element could be driven by a desired appearance of the toothpick, preference by the user or manufacturer, and/or type of application (e.g. area of treatment or location of treatment). FIG. 6 shows an example of a toothpick 600 with a handle 610 and an element 620, whereby element 620 could have a pre-arranged angle 630 or the angular position 630 could be formed by bending or shaping element 620. Switch 640 could be used to control the light source as discussed supra. However, in another aspect switch 640 might control the angular position of the element through for instance a heating mechanism, shape memory alloys, mechanical means, or the like. FIG. 7 shows an example of a toothpick 700 with a handle 710 and an element 720, whereby element 720 includes a bead shape 730 at the tip of element 720. The radiation of light beams 740 will now pass through element including through bead shape 730. FIG. 8 shows an example of a toothpick 800 with a handle 810 and an element 820, whereby element 820 includes a flat shaped head 830 towards the end of element 820. The radiation of light beams 840 will now pass through element including through flat shaped head 830. Different shapes or heads could be developed with different sizes and as discussed infra with different texture, all which are primarily dependent on the type of application and/or user preference. The size of these additional shapes could alter the dimensions discussed supra with reference to FIGS. 4–5.

Figure 9:
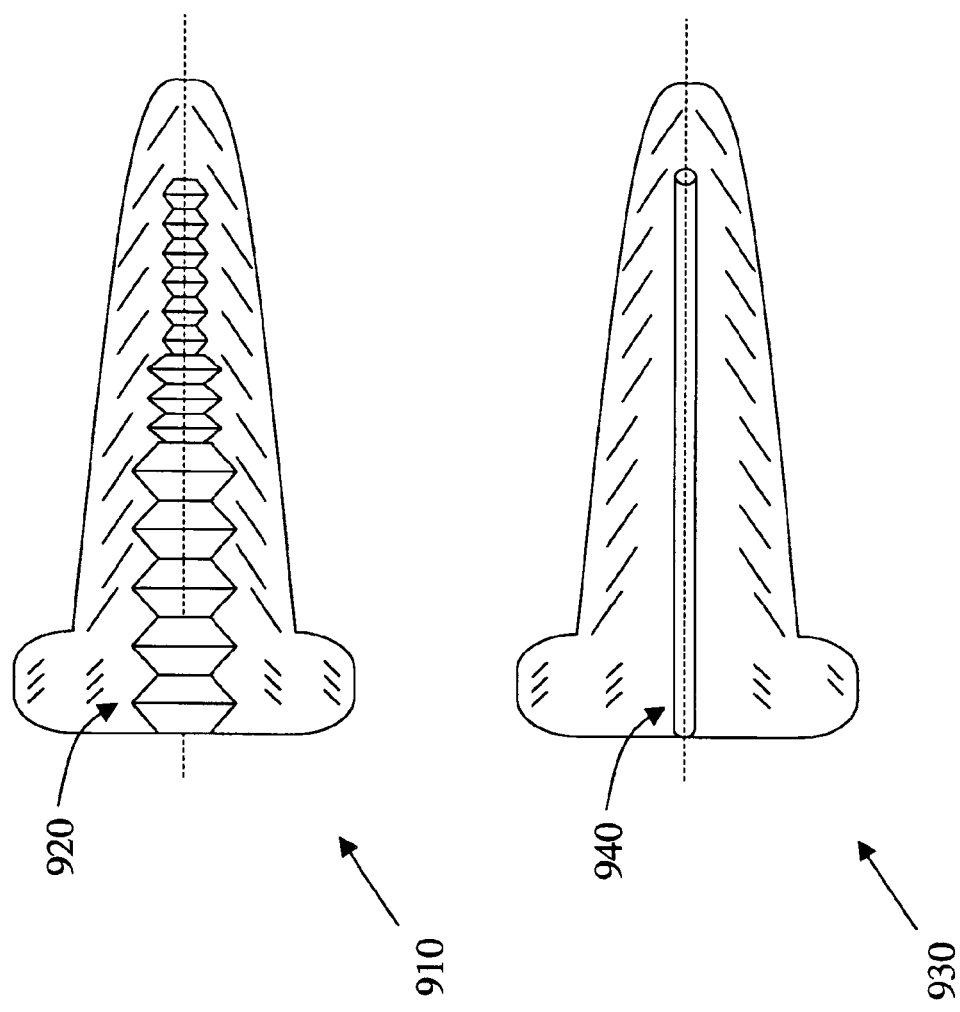
FIGS. 9–10 show examples of elements with optical components according to the present invention.
Figure 10:
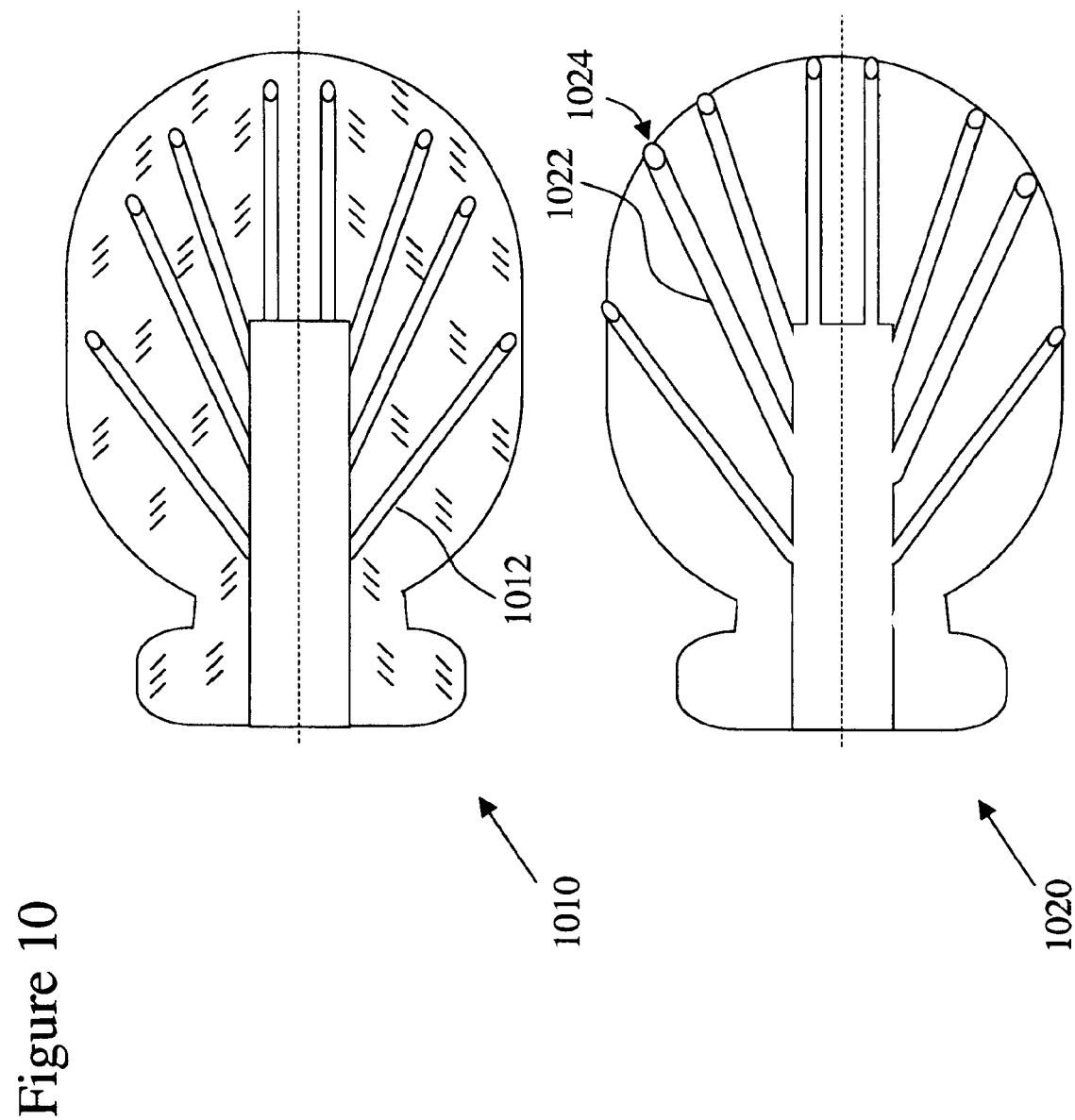

The inside of element could include one or more optical components to direct and propagate a light beam through a transparent element and through the surface of that element. As a person of average skill in the art to which this invention pertains would readily appreciate, this could be accomplished in different ways. For instance, one could include optical guide(s) or path(s), optical fiber(s), lens(es), mirror(s), prism(s), reflective coating(s), reflective groove(s), beam splitter(s), collimator(s), light channel(s) and grating(s). In the example of FIG. 9, transparent element 910 includes reflective grooves 920 to promote the propagation of light beam in such a way that it is able to pass through transparent element 910 in various directions (slanted lines indicate a transparent element as shown by element 910, 930). Transparent element 930 shows an example of a single optical guide 940 from which the light beam radiates outward in various directions through the transparent element 930. An optical guide could be a hollow guide (air filled) or a guide filled with a material (e.g. water, a gel or a silicone) that optically guides a light beam and propagates the light beam through the transparent element. FIG. 10 shows an example of an element 1010 with a flat shaped head that includes multiple optical guides 1012 integrated with a transparent element (slanted lines indicate a transparent element). Element 1020 is an example whereby multiple optical guides 1022 open up 1024 through the surface of element 1020. Note that the material of element 1020 is not transparent and therefore the light beam passes only through openings 1024 of optical guides 1022 at a body surface. The element could therefore include various openings positioned anywhere over the surface of the element.

It has been shown that effect of radiation is improved in combination with massaging the tissue. Pressuring alive soft tissue causes an increase in its transparacy thereby providing for better penetration of the radiation (See G A Askaryan (1982) in a paper entitled *"The increasing of transmission of laser and other radiation through the sift turbid physical and biological media"* and published in "Kvantovaya Electronika, V9(N7):1370–1383). The present invention generalizes this concept. Accordingly, the present invention could include a massaging means to massage the body structure(s) and improve the transparency to the light beams. A first aspect of applying a massaging means relates to the movement of the element or the pressure of the element against the body structures will apply a massaging effect.

Figure 11:
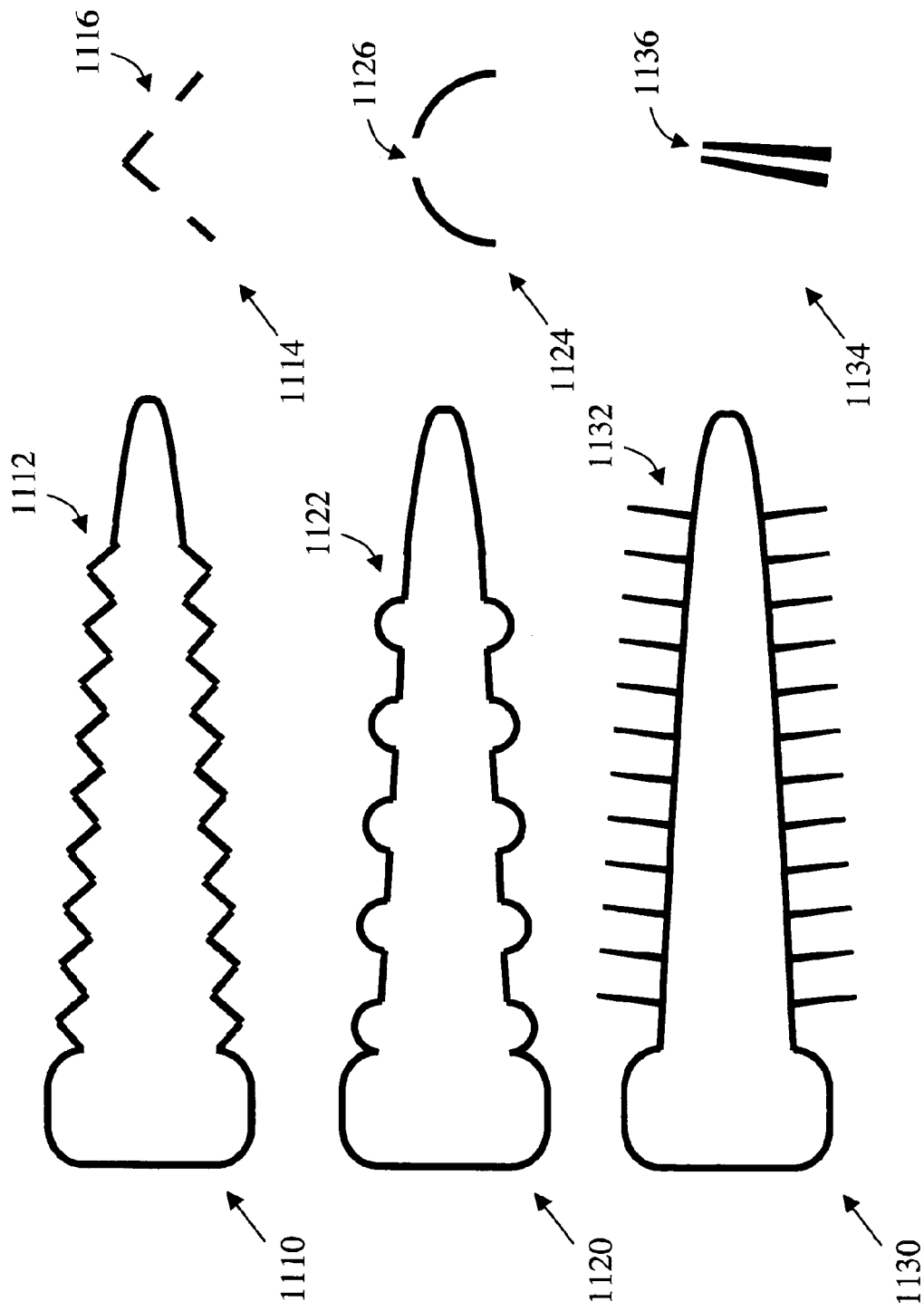
FIG. 11 shows elements with a textured surface or bristles according to the present invention.

In a second aspect, adding texture or bristles to the surface of the element could provide a massaging means. FIG. 11 shows examples in which element 1110 includes a ribbed surface 1112, element 1120 includes a bubbled surface 1122, and element 1130 includes bristles 1132. In light of the discussion supra with regards to transparent or non-transparent material for the element, each added texture or bristle could have openings or optical guides or openings 1114, 1124, 1134 to allow passage of the light beam through ribbed element 1116, bubbled element 1126, bristle 1136, respectively. Furthermore, the ribbed element, bubble element or bristle could also be transparent to the selected light beam.

The texture or bristles could be positioned in any position or direction with respect to the handle. For instance, bristles could be positioned more or less perpendicular to the element or bristles could be positioned under an angle with respect to the element. The direction of the texture or bristles could depend on the type or shape of the element or the type of massaging effect that would be desired. The type and size of texture or bristles is dependent on the type of body structure. It would however be preferred to have soft texture or bristles that do not irritate or damage the body structures. However, in another aspect it might be desired to have firm texture or bristles. The bristles could for instance be made out of nylon, soft fiber, or any synthetic blend. Using the texture or bristles to add a massaging effect is accomplished in a similar fashion as a toothbrush or a brush.

Figure 12:
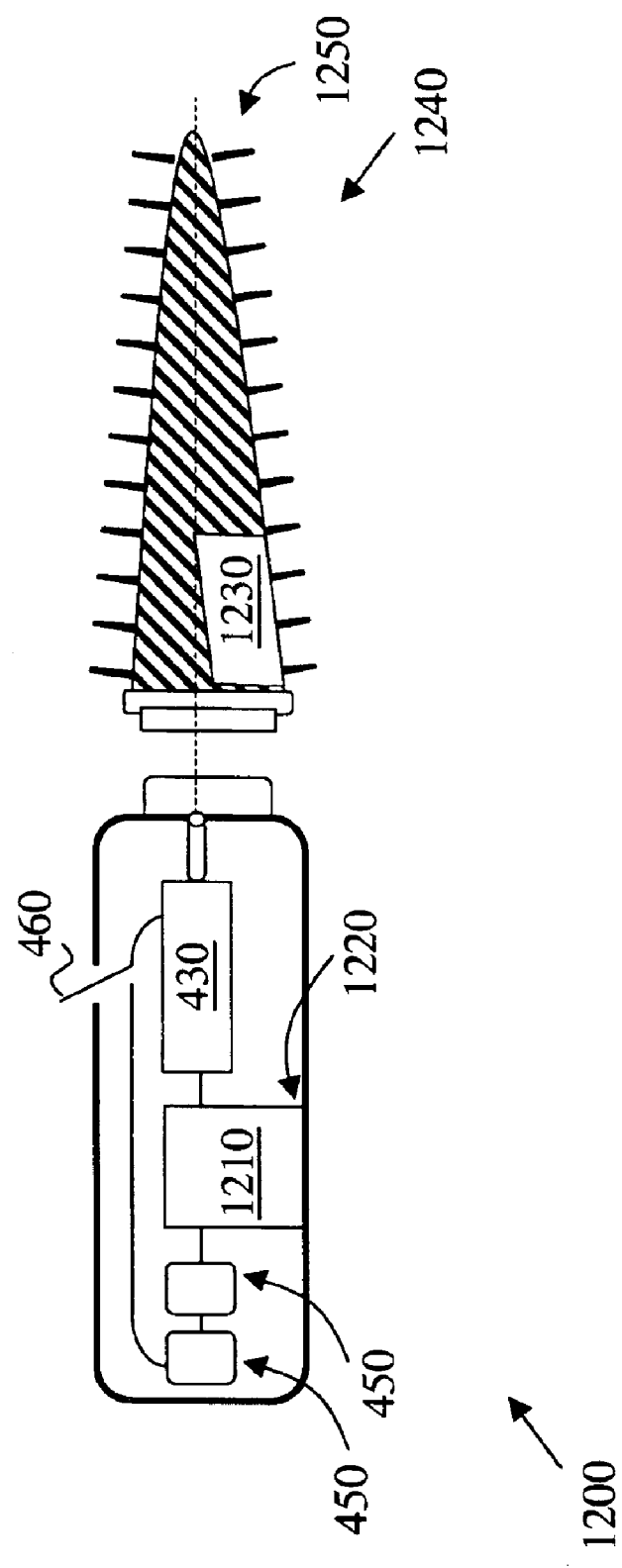
FIG. 12 shows a toothpick with vibration means according to the present invention

In another aspect, the massaging means of the present invention could include be a vibrating means to massage body the structures. Examples of such a vibrating means that could be used are an ultrasonic means, a piezoelectric means or a mechanical means. Such vibrating means are known in the art. FIG. 12 shows a handle 1200 with a vibrating means 1210. Since vibrating means 1210 is positioned against the inner edge 1220 of handle 1200, the entire handle 1200 might vibrate. It would also be feasible to position a vibrating means 1230 inside the element 1240; however in this case one needs to make sure that such a vibrating means would get in the way of the light beam path. In yet another aspect, vibrating means 1230 could be connected to the bristles 1250 or even the texture, i.e. to vibrate the bristles or texture to provide an additional massaging effect to the massaging effect established by the bristles through movement as described supra.

Figure 13:
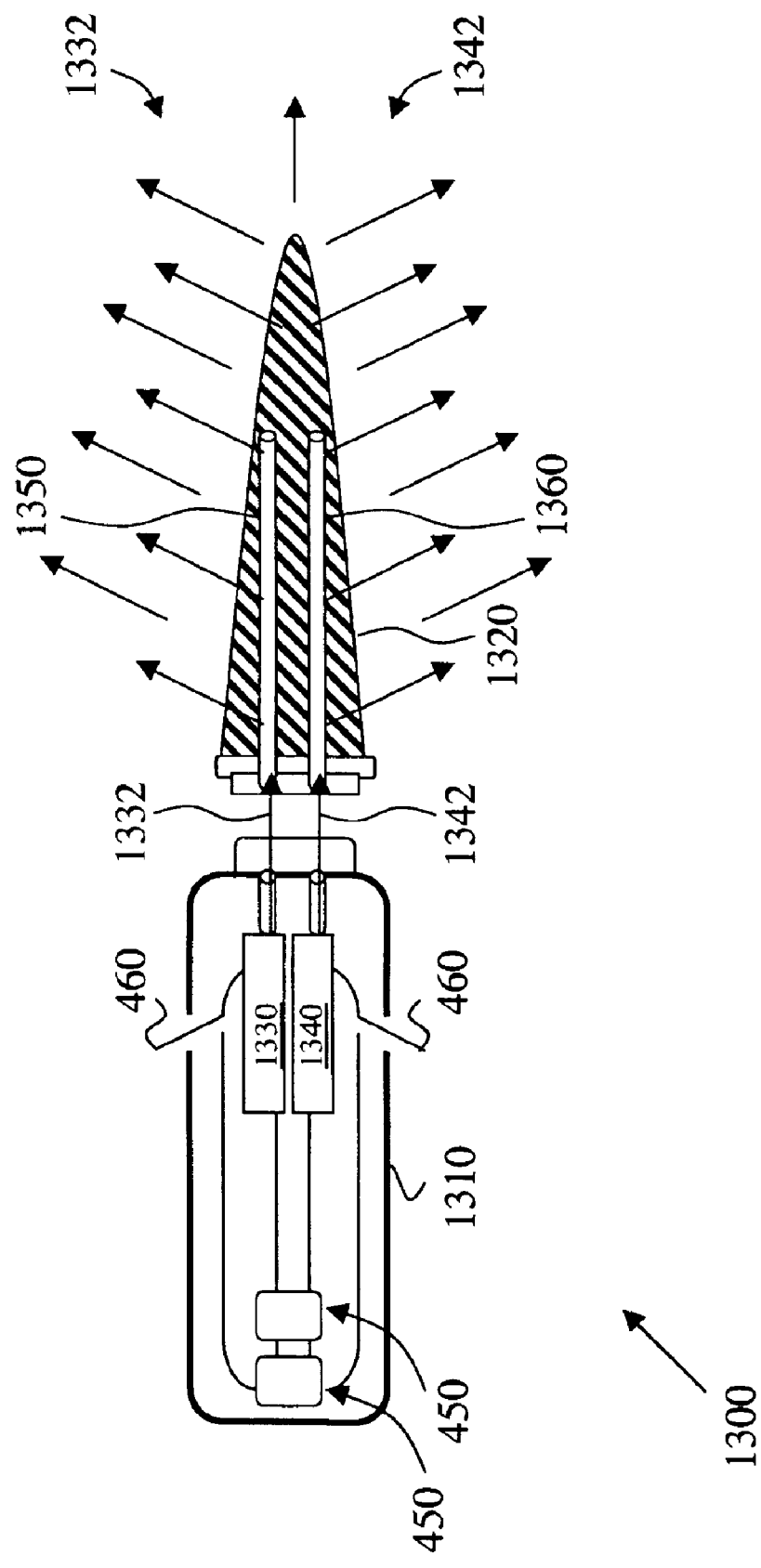
FIG. 13 shows a toothpick with multiple light sources according to the present invention.

As discussed supra, more than one light treatment could be concurrently delivered (See FIGS. 1–3). FIG. 13 shows an example of a toothpick 1300 with a handle 1310 and a transparent element 1320. The exemplary toothpick 1300 is capable of engaging two light sources 1330, 1340 each with a unique light beam and light treatment 1332, 1342. Each light source 1330, 1340 is optically connected to transparent element 1320. Furthermore, transparent element 1320 could include optical guides 1350, 1360 to promote the propagation of each light beam 1332, 1342.

Figure 14:
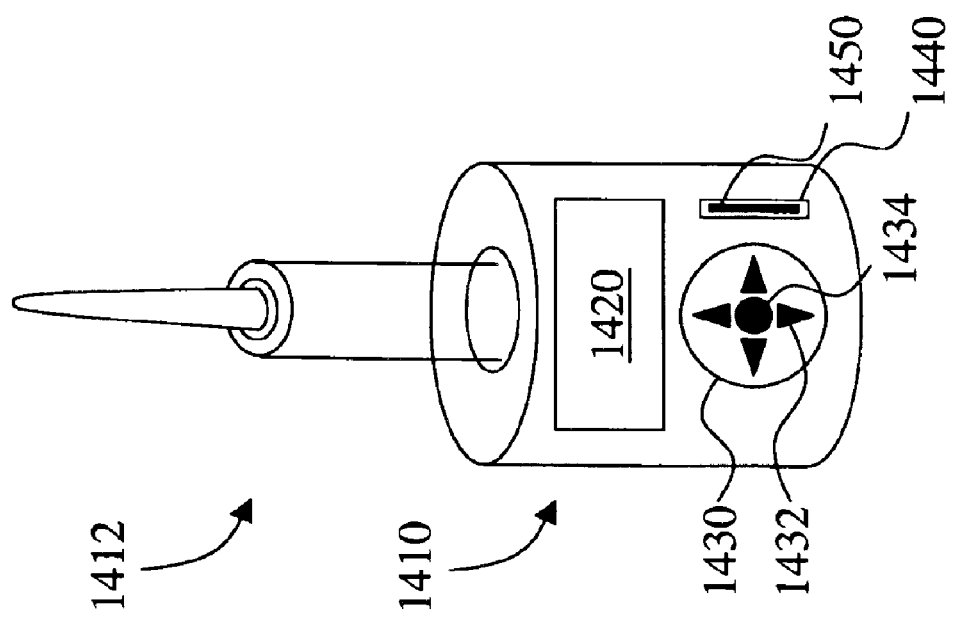
FIG. 14 shows a toothpick stored in a cradle according to the present invention.

FIG. 14 shows a cradle 1410 that can be used to store the toothpick 1412. Cradle 1410 could also be used as a power supply (re)-charging device. Cradle 1410 could include a selection means 1430 for a user to select the hygienic effect(s) or treatment parameter(s) related to the unique hygienic effect(s). Selection means 1430 could be a selection means with, for instance, four arrow buttons 1432 and one center button 1434. Each arrow button 1432 corresponds to a function or selection that could be selected from a displaying means 1420. The up, down, left and right arrow buttons could relate to the browsing or selection from displaying means 1420. Displaying means 1420 could be any type or size of displaying means that would fit the cradle and is useful to the user. Necessary software and hardware components would be included to provide the functionality to display the parameters, selections and/or functions as well as provide functionality to the buttons. Center button 1434 could be used as the enter button to confirm a selection as is common in the art. The cradle could include different variations of a selection means and is not limited to the selection means shown by 1430.

Cradle 1410 could also include a slot 1440 for a read/writer card 1450 to read or write data. Examples of read/writer card 1450 are for instance a memory stick, compact flash card, smart media card, secure digital card, multi media card, microdrive or the like, which are common in the art. Read/writer card 1450 can upload information to the toothpick, store information from the toothpick, and could be interactively used with any type of hygienic service provider as described infra.

Figure 15:
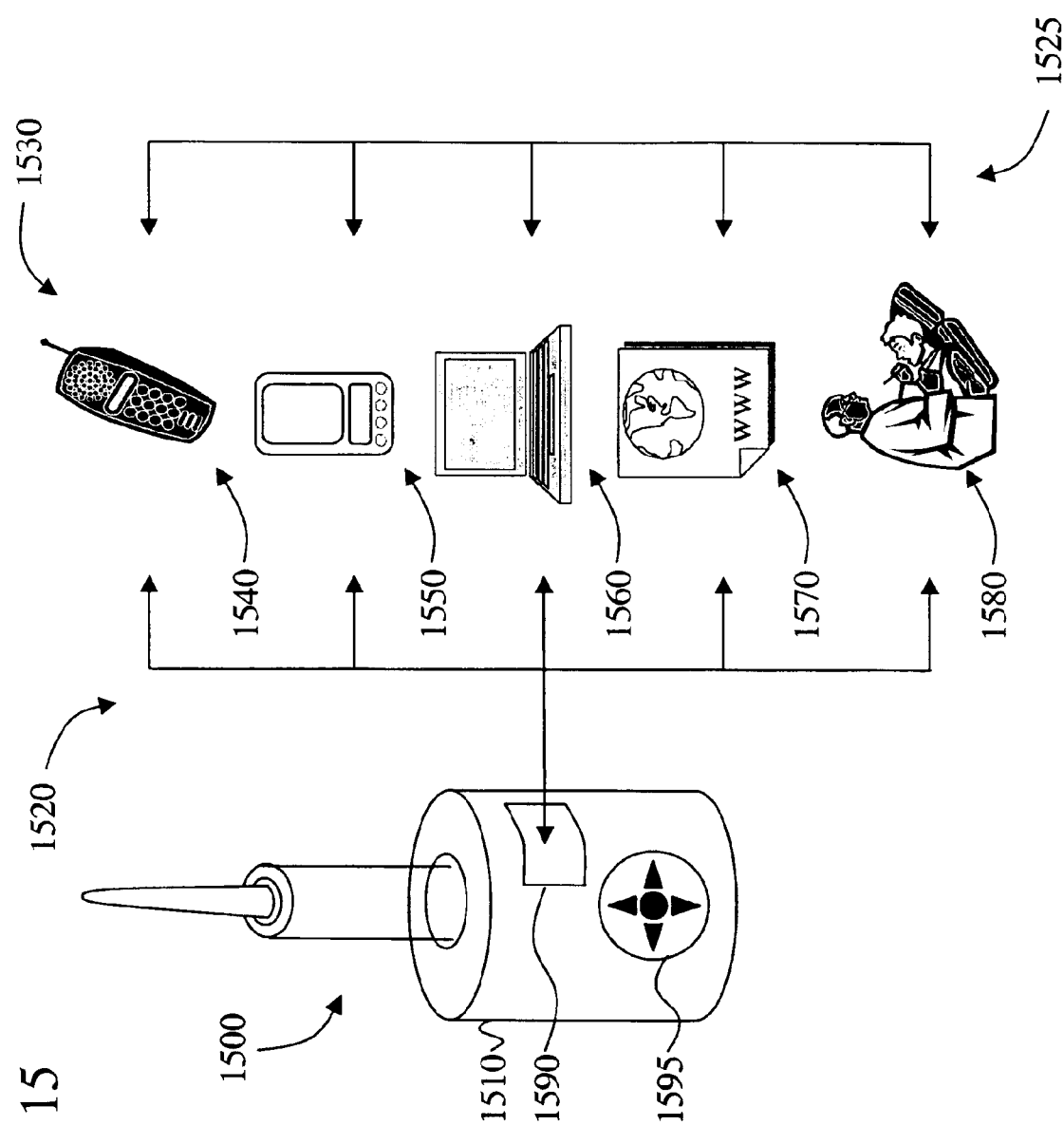
FIG. 15 shows a toothpick stored in a cradle communicating with hygienic service providers according to the present invention.

FIG. 15 shows a toothpick 1500 positioned in a cradle 1510 that could communicate 1520 with a hygienic service provider 1530. Hygienic service provider 1530 includes a cell phone 1540, a personal digital assistant, a Pocket PC or a handheld communication device (all three shown by 1550), a computer 1560, an Internet website 1570 or a professional service 1580 (e.g. a dentist, a medical doctor, a pharmaceutical company, medical company, or the like). The hygienic service provider 1530 provides information related to the toothpick 1500 that could be communicated 1520 back and forth between toothpick 1500 and hygienic service provider 1530. Furthermore, the individual hygienic service providers 1530 could interact and communicate with each other 1525. For instance, one could use Internet website 1570 and relay the data to cell phone 1540 before communicating with toothpick 1500. Several different scenarios are possible and would provide flexibility to the user to obtain and provide data related to their hygienic treatment(s) that are used by toothpick 1500. The communications means that could be used includes any wireless or wired communication means as common and available in the art. Furthermore, toothpick 1500 could include IR port, RF link, Bluetooth, phone line or Ethernet port or any type of wireless or wired communication means (shown by 1590) suitable to communication with hygienic service provider 1530. Selection means 1595 could be used as a means to send data from toothpick 1500 to hygienic service provider 1530 in a similar fashion as the HotSync key on Personal Digital Assistants (PDAs). Read/writer card 1450 as shown in FIG. 14 could also be used as communication means 1520, 1525.

Figure 16:
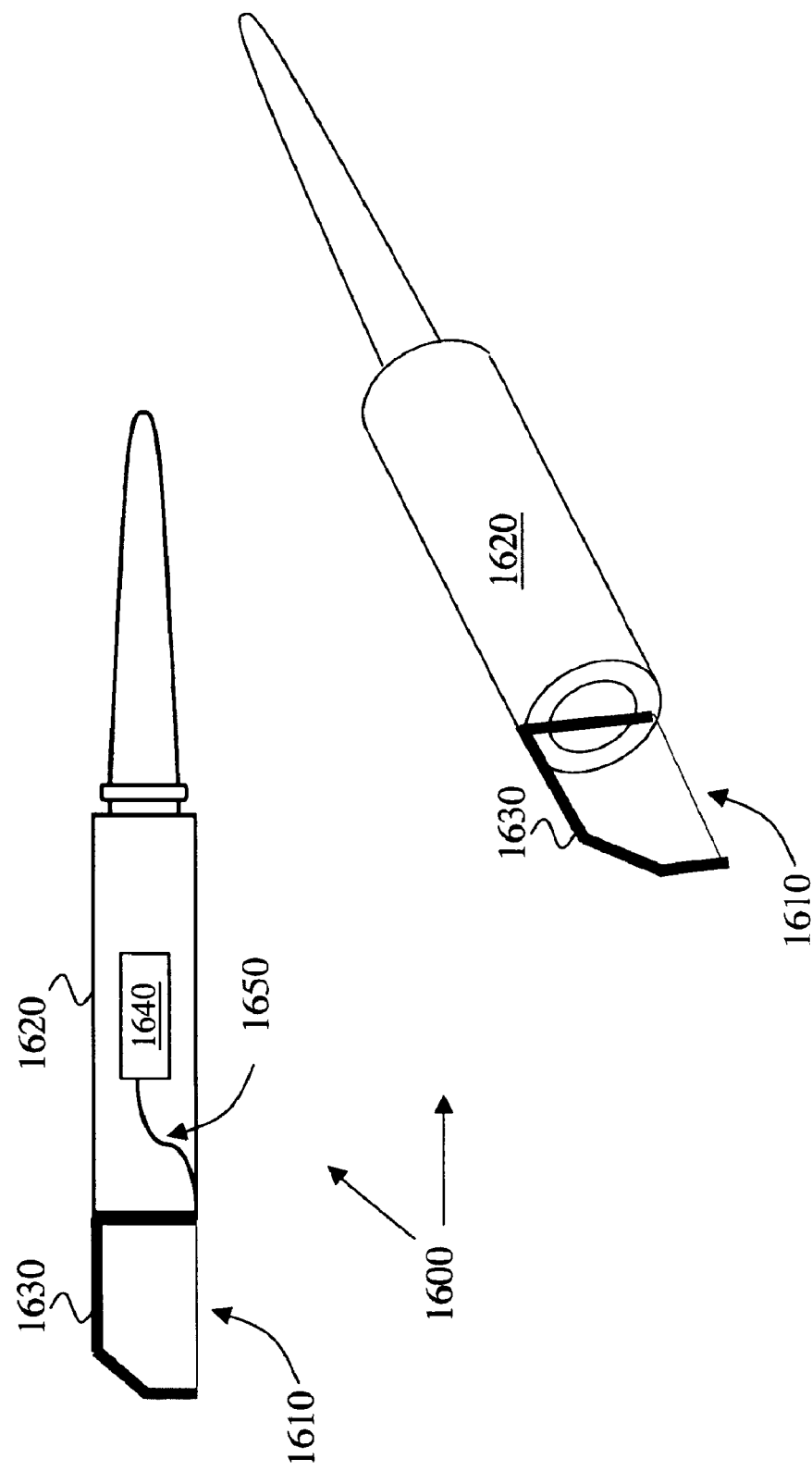
FIG. 16 shows a toothpick with a floss according to the present invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. In one variation as shown in FIG. 16, a floss 1610, e.g. a dental floss, could be added to a toothpick 1600 of the present invention. The floss could for instance be added at the bottom of a handle 1620, however it could also be added to the side of handle 1620. The floss is kept in place for instance by a soft plastic or any other holder mechanism 1630 as common in the art. The floss could be optically connected 1650 to a light source 1640, by similar means as discussed supra for the optical connection between the light source and the element. This could be a separate light source with its own control or could be the same light source as for the element. In case a different light source is used for the floss, there is a choice whether the same or a different light treatment for the floss could be used compared to the light treatment for the element. In any event, the floss would glow when illuminated by a light beam from light source 1640.

In another variation an agent could be used and applied to the body structures before, during or after the application of the light treatment. Examples of agents are for instance bioprotective agents, photocatalyst, treatment gels or cream, soothing agents, skin permeation enhancers or the like (See, for instance, the following companies/products which are listed for purposes of illustration and should not be regarded as limiting to the invention: Neova by Procyte Corp. www-.procyte.com; Medicalia Inc. www.medicalia.com; or ESBA Laboratories Inc.). Such agents could work as a catalyst, soother or enhancer to the body structures. All such variations are considered to be within the scope and spirit of the present invention as defined by the following claims and their legal equivalents.

What is claimed is:

1. A toothpick for light treatment at a body structure, comprising:
   (a) a handle, wherein said handle comprises two or more light sources each capable of delivering a unique light beam, wherein said unique light beam provides a unique light treatment; and
   (b) an element optically connected to said light source, wherein said element is slender and elongated, and wherein said light beam radiates through the surface of said element at said body structure, said radiation is not limited to radiation through the tip of said element.

2. The toothpick as set forth in claim 1, wherein said element is a transparent element and said light beam radiates substantially through the entire surface of said transparent element.

3. The toothpick as set forth in claim 1, further comprising one or more optical guides and said light beam radiates through said one or more optical guides.

4. The toothpick as set forth in claim 1, wherein said element is tapered.

5. The toothpick as set forth in claim 1, wherein the end of said element comprises a bead shape.

6. The toothpick as set forth in claim 1, wherein said element comprises a flat shaped head.

7. The toothpick as set forth in claim 1, wherein the surface of said element comprises texture.

8. The toothpick as set forth in claim 1, wherein said element further comprises bristles.

9. The toothpick as set forth in claim 8, wherein said bristles are transparent to said light beam.

10. The toothpick as set forth in claim 1, wherein said handle is a removable, a disposable, a reusable or a replaceable handle or said element is a removable, a disposable, a reusable or a replaceable element.

11. The toothpick as set forth in claim 1, wherein said element comprises a soft plastic, a silicone or a latex.

12. The toothpick as set forth in claim 1, wherein said element is bendable or formable.

13. The toothpick as set forth in claim 1, wherein said element has a pre-arranged angle.

14. The toothpick as set forth in claim 1, wherein each of said two or more light sources is a low power laser, a light emitting diode or a semiconductor laser.

15. The toothpick as set forth in claim 1, wherein said light treatment is selected from the group consisting of an anti-inflammatory effect, a preventative effect, an anti-bacterial effect, a sterilizing effect, a heating effect, a caries-protective effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect.

16. The toothpick as set forth in claim 1, wherein said light beam comprises light from the ultraviolet, visible or infrared spectrum.

17. The toothpick as set forth in claim 1, wherein said body structure comprises a naturally created body structure, a wound, or a surgically created body structure.

18. The toothpick as set forth in claim 1, wherein said light beam is applied in a manner selected from the group consisting of a pulsed manner and a continuous manner.

19. The toothpick as set forth in claim 1, further comprising one or more optical components wherein said one or more optical components are selected from the group consisting of optical guides or paths, optical fibers, lenses, mirrors, prisms, reflective coatings, reflective grooves, beam splitters, collimators, light channels and gratings.

20. The toothpick as set forth in claim 1, further comprising a massaging means to massage said body structure.

21. The toothpick as set forth in claim 1, further comprising a floss.

22. The toothpick as set forth in claim 21, wherein said floss is a transparent floss and wherein said floss is optically connected to
at least one of said light beams or said floss is optically connected to a different light beam of a different light source.

23. A toothpick for light treatment at a body structure, comprising:
(a) a handle, wherein said handle comprises a light source capable of delivering a light beam, wherein said light beam provides said light treatment;
(b) an element optically connected to said light source, wherein said element is slender and elongated, wherein said light beam radiates through the surface of said element at said body structure; and
(c) a floss.

24. The toothpick as set forth in claim 23, wherein said handle comprises two or more lights sources each delivering a unique light treatment.

25. The toothpick as set forth in claim 23, wherein said element is tapered, flat shaped or comprises a bead shape end.

26. The toothpick as set forth in claim 23, wherein the surface of said element comprises texture, bristles, or transparent bristles to said light beam.

27. The toothpick as set forth in claim 23, wherein said handle is a removable, a disposable, a reusable or a replaceable handle or said element is a removable, a disposable, a reusable or a replaceable element.

28. The toothpick as set forth in claim 23, wherein said element is bendable, formable, or has a pre-arranged angle.

29. The toothpick as set forth in claim 23, wherein said light source is a low power laser, a light emitting diode or a semiconductor laser.

30. The toothpick as set forth in claim 23, wherein said light treatment is selected from the group consisting of an anti-inflammatory effect, a preventative effect, an anti-bacterial effect, a sterilizing effect, a heating effect, a caries-protective effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect.

31. The toothpick as set forth in claim 23, wherein said light beam comprises light from the ultraviolet, visible or infrared spectrum.

32. The toothpick as set forth in claim 23, wherein said light beam is applied in a manner selected from the group consisting of a pulsed manner and a continuous manner.

33. The toothpick as set forth in claim 23, further comprising one or more optical components wherein said one or more optical components are selected from the group consisting of optical guides or paths, optical fibers, lenses, mirrors, prisms, reflective coatings, reflective grooves, beam splitters, collimators, light channels and gratings.

34. The toothpick as set forth in claim 23, further comprising a massaging means to massage said body structure.

35. The toothpick as set forth in claim 23, wherein said floss is a transparent floss and wherein said floss is optically connected to said light beam of said light source or said floss is optically connected to a different light beam of a different light source.

36. A method to optically apply two or more unique light treatments at a body structure, comprising the steps of:
(a) optically connecting an element to two or more light sources each capable of delivering a unique light beam, wherein said light beam provides a unique light treatment, wherein said light beams radiate through the entire surface of said element; and
(b) positioning said element with respect to said body structure to apply said light treatments at said body structure.

37. The method as set forth in claim 36, further comprising the step of providing a handle to host said light source and said handle is disposably or resuasably attached to said element.

38. The method as set forth in claim 36, further comprising the step of bending or forming said element.

39. The method as set forth in claim 36, wherein said element is provided in a pre-arranged angle.

40. The method as set forth in claim 36, wherein the relative location of said element with respect to said body structure is varied, and therewith varying the application of said light treatments provided by said two or more light sources with respect to said body structure to achieve blending of said light treatments at said body structure.

41. The method as set forth in claim 36, wherein said light treatment is selected from the group consisting of an anti-inflammatory effect, a preventative effect, an anti-bacterial effect, a sterilizing effect, a caries-protective effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect.

42. The method as set forth in claim 36, further comprising the step of adding an agent to said body structure.

43. The method as set forth in claim 36, further comprising the step of massaging said body structure with said element.

44. The method as set forth in claim 36, further comprising the step of providing a massaging means to massage said body structure.

45. The method as set forth in claim 36, further comprising the step of adding a floss and using said floss to floss said body structure.

46. The method as set forth in claim 45, wherein said floss is a transparent floss and further comprising the step of optically connecting said transparent floss to at least one of said light beams or optically connecting said transparent floss to a different light beam of a different light source.

* * * * *